US008002721B2

(12) United States Patent
Bretl et al.

(10) Patent No.: US 8,002,721 B2
(45) Date of Patent: Aug. 23, 2011

(54) THERMAL COVERING

(75) Inventors: Donald Stephen Bretl, West Chester, OH (US); Mary Elaine Freeland, Loveland, OH (US); Kyle William Harris, Maineville, OH (US); Richard W. Pack, Blue Ash, OH (US); Angela Marie Reed, Mason, OH (US)

(73) Assignee: Wyeth LLC, Madison, NJ (US)

(*) Notice: Subject to any disclaimer, the term of this patent is extended or adjusted under 35 U.S.C. 154(b) by 0 days.

(21) Appl. No.: 11/899,654

(22) Filed: Sep. 7, 2007

(65) Prior Publication Data

US 2008/0064996 A1 Mar. 13, 2008

Related U.S. Application Data

(60) Provisional application No. 60/843,119, filed on Sep. 8, 2006.

(51) Int. Cl.
*A61F 5/00* (2006.01)
(52) U.S. Cl. .................... 602/2; 602/20; 602/21; 602/22
(58) Field of Classification Search ................ 602/2, 14, 602/20–22; 2/158–161.1; 607/108, 111, 607/114
See application file for complete search history.

(56) References Cited

U.S. PATENT DOCUMENTS

| 4,706,658 | A | 11/1987 | Cronin |
| 5,415,624 | A | 5/1995 | Williams |
| 6,141,801 | A * | 11/2000 | Helenick ........................... 2/159 |
| 6,505,349 | B1 * | 1/2003 | Logan et al. ...................... 2/158 |
| 7,043,768 | B2 * | 5/2006 | Gogarty ......................... 2/161.1 |
| 2003/0109910 | A1 | 6/2003 | Lachenbruch et al. |
| 2004/0147990 | A1 | 7/2004 | Graham et al. |
| 2007/0106353 | A1 * | 5/2007 | Carstens ....................... 607/112 |

FOREIGN PATENT DOCUMENTS

DE 24 57 193 A1 6/1976
WO WO 99/47011 A 9/1999

OTHER PUBLICATIONS

International Search Report, Jun. 3, 2008.

* cited by examiner

*Primary Examiner* — Michael A. Brown
(74) *Attorney, Agent, or Firm* — Joel Silver; Jeffrey M. Gold (57) ABSTRACT

The present invention is directed to a thermal covering that delivers consistent therapy to a portion of a user's hand-wrist area, is easy to use and apply to the body, and is securely positionable on the body. The thermal covering can be entirely disposable after one use. The thermal covering can also have a disposable component and a reusable component that can be packaged individually together as a kit.

13 Claims, 9 Drawing Sheets

THERMAL COVERING

CROSS REFERENCE TO RELATED APPLICATIONS

This application claims the benefit of U.S. Provisional Application No. 60/843,119, filed on Sep. 8, 2006.

FIELD OF THE INVENTION

The present invention is directed to devices used to deliver heat to a painful joint or other body part. Particularly the invention is directed to a covering for the hand and wrist areas. Most particularly the invention is directed to a thermal covering to deliver heat or cold to the hand and/or wrist.

BACKGROUND OF THE INVENTION

A common method of treating temporary or chronic pain is by application of heat or cold to the afflicted area. Such heat treatments are used as a means of therapy for conditions which include aches, stiffness in muscles and joints, nerve pain, rheumatism, arthritis, and the like. Typically, the method for relieving pain using heat treatments has been topical application of relatively high heat, e.g., greater than about 40° C. for a short period of time, e.g., from about twenty minutes to about one hour.

Elastic compression wrap bandages have been used to help stabilize afflicted areas during injury healing. Heating pads, whirlpools, hot towels, hot water bottles, hot packs, cold packs and the like have been commonly used to apply heat or cold to an area to relieve the pain of aches, stiffness in muscles and joints, nerve pain, rheumatism, arthritis, and the like. However, many of these devices are inconvenient for use on a regular and extended basis because for example the heat energy may not be immediately available when needed or may not be released in a controllable manner. That is, many of the thermal units or devices do not provide long lasting heat and also do not maintain a consistent temperature over long periods of time. Proper positioning of the thermal energy also may not be maintainable during joint flexure or other body movement. In general, the beneficial therapeutic effects from the administration of heat diminish after the heat source is removed—thus movement or flexion of a joint or body part may remove the heat source from contact with the joint or body part and thereby reduce the effectiveness of the device.

Various thermal devices are known, such as heat packs based on iron oxidation. However, such devices have not proven satisfactory because many of these devices are bulky, cannot maintain a consistent and controlled temperature, present difficulty staying in place during use, and/or have unsatisfactory physical dimensions that hinder their efficacy, and they must be thrown away after one use. Specifically, such devices cannot be easily incorporated into wraps that comfortably and reliably conform to various body contours. Hence they deliver inconsistent, inconvenient and/or uncomfortable heat application to the body.

Recently, improved disposable body wraps have been described in such documents as U.S. Pat. Nos. 5,728,057; 5,728,058; 5,860,945; 6,048,326; 5,728,146; 5,735,889; 6,102,937; 6,123,717; 5,925,072; 6,074,413; 5,741,318; 5,980,562; 5,674,270; 5,837,005; 6,096,067; 6,019,782; 5,906,637; 6,024,761; 5,904,710; and 6,336,935; WO 98/29064; WO 97/01312; WO 97/01310; WO 97/49361; WO 98/29063; WO 99/09917; WO 99/09918; and WO 01/19302. These documents disclose disposable body wraps comprising a plurality of heat cells, wherein the body wraps deliver consistent, long-lasting thermal treatment to the afflicted area of the body. The wraps described in these documents, and the technology incorporated therein, have provided important advances in the art.

Recently, wraps such as HEAT ZONE®, commercially available from AccuFitness, Englewood, Colo., have been provided that contain a "semi-durable" (i.e. partly reusable, or reusable for a limited number of uses) body wrap having a pocket for the placement of a single "heat pad" containing an exothermic composition. While these products diminish the disposable nature of the overall product, and thus may be more economical than full disposable devices, the heat pads are subject to movement and displacement when contained in the pocket. This results in decreased efficacy and utility of the overall wrap because it fails to consistently deliver efficacious heat therapy to the area in need of treatment.

Thus, with many known disposable, reusable and partially reusable wraps, it is particularly difficult to get consistent heat applied to the hand and wrist area. Such wraps are particularly disadvantageous for those having arthritis in the hand and wrist area, and particularly the thumb. The thumb is a crucial digit necessary for most daily functions, and is often particularly painful when injured or arthritic. Yet it is difficult to effectively apply and retain heat to the thumb with many of the known therapeutic thermic devices. In addition, many known thermic devices are particularly difficult for a user with injured or arthritic hands to apply to their own bodies. Therefore, it would be desirable to provide economical disposable, reusable, and/or partly reusable thermal devices that provide secure, consistent, long-lasting application of heat to the hand-wrist area, while particularly providing heat to the thumb area and being easy for a user with injured or arthritic hands to apply.

SUMMARY OF THE INVENTION

The present invention is directed to a thermal covering that delivers consistent therapy to a portion of a user's body, is easy to use and apply to the body, and is securely positionable on the body. The thermal covering of the present invention can be entirely disposable. Alternatively, the thermal covering can also have a disposable or reusable thermic component and a reusable chassis component. The device of the present invention is particularly useful for the hand-wrist area, including the thumb. The present invention also includes methods of using the thermal covering(s), and kits containing the covering(s).

An embodiment of the invention is a thermal covering for use on the hand-wrist area of a user comprising:
  (a) a chassis having a longitudinal axis and a transverse axis and comprising a flexible body portion having at least one thermal region;
  (b) a thermic component attachable to the body portion at the thermal region; and
  (c) a digit-receiving aperture through the body portion and adjacent to the thermal region.

The present invention is further directed to methods of treating pain selected from acute muscular, acute skeletal, acute referred, recurrent muscular, recurrent skeletal, recurrent referred, chronic muscular, chronic skeletal, chronic referred pain, and combinations thereof, comprising applying the foregoing thermal covering to the area in need of treatment.

The present invention is also directed to kits comprising a reusable chassis and at least one reusable or disposable thermic component. The thermic component of the present invention can comprise at least one separately disposable heat pack containing an exothermic composition; reusable heatable and reheatable thermic components; battery powered thermic components; electric powered thermic components; electromechanical thermic components; moisture-generating thermic components; and combinations thereof.

With embodiments having a reusable chassis and a disposable or reusable thermic component, continued use of the reusable chassis is possible, with interchange of various disposable and/or reusable thermic components.

Thus, the presently inventive devices, methods, and kits provide advantages relative to those provided in the art. Indeed, the present devices, methods, and kits provide thermal coverings which consistently deliver heat or cold to the area in need of treatment, particularly the hand-wrist area, including the thumb. These and other aspects of the present invention are described in further detail herein.

BRIEF DESCRIPTION OF THE DRAWINGS

While the specification concludes with claims that particularly point out and distinctly claim the present invention, it is believed that the present invention is further understood from the following description of alternative embodiments, taken in conjunction with the accompanying drawings, wherein:

DETAILED DESCRIPTION OF THE INVENTION

All percentages and ratios are calculated by weight unless otherwise indicated.

Referenced herein may be trade names for components including various ingredients utilized in the present invention. The inventors herein do not intend to be limited by materials under a certain trade name.

Equivalent materials (e.g., those obtained from a different source under a different name or reference number) to those referenced by trade name may be substituted and utilized in the descriptions herein.

In the description of the invention various embodiments and/or individual features are disclosed. As will be apparent to the ordinarily skilled practitioner, all combinations of such embodiments and features are possible and can result in preferred executions of the present invention.

As used herein, the term "mammal" means vertebrate mammals. Non-limiting examples of mammals are humans and companion animals (e.g., domestic cats, dogs, horses, cows, or other similar animals). Exemplary mammals are humans.

As used herein, the term "plurality" with reference to a given noun means more than one, alternatively more than two, alternatively more than three, and alternatively more than four units of the given noun.

As used herein "attachable" means that a component is releasably attachable as defined herein, permanently attachable as defined herein, and/or formed integrally and irreversibly into a component.

The devices, methods, and kits herein may comprise, consist essentially of, or consist of any of the elements as described herein.

While various embodiments and individual features of the present invention have been illustrated and described herein, various other changes and modifications can be made without departing from the spirit and scope of the invention. As will also be apparent to the ordinarily skilled practitioner, all combinations of the embodiments and features taught in the foregoing disclosure are possible and can result in preferred executions of the invention.

Each of the individual elements of the invention, as well as alternative, optional embodiments, is described further below.

The Chassis

The thermal covering of the present invention comprises a chassis. The chassis of the present invention comprises a longitudinal axis and a transverse axis; a flexible body portion having at least one thermal region; wherein the body portion comprises a digit-receiving aperture through the body portion and adjacent to the thermal region.

Additionally, the thermal covering can comprise at least one flexible retaining element, such as a strap. Additionally, at least one of the body portion and the flexible retaining element comprises an elastomeric material; and wherein at least one of the body portion and the flexible retaining element is stretchable along the longitudinal axis of the chassis.

Because some alternative embodiments herein comprise thermic components comprising at least about one heat cell comprising exothermic or endothermic compositions, the material of the chassis can be permeable to air. The chassis material can be permeable to air in order that it does not inhibit any exothermic or endothermic reaction within the thermic component.

The chassis can comprise materials including but not limited to ACE® bandage or wrap materials (commercially available from Becton Dickenson of Franklin Lakes, N.J.), or another like bandage or wrap. Alternatively, the chassis can include combinations or layers of material including but not limited to, films or films laminated to non-woven fabrics. Films, if used, are those having heat sealability and which are capable of being easily thermally fused. Non-wovens, if used, provide support and integrity to film layer substrates. Non-limiting examples of suitable films include polyethylene, polypropylene, nylon, polyester, polyvinyl chloride, polyvinylidiene chloride, polyurethane, polystyrene, saponified ethylene-vinyl aceate copolymer, ethylene-vinyl acetate copolymer, natural rubber, reclaimed rubber, synthetic rubber and combinations thereof. Non-limiting examples of suitable non-wovens include nylon, rayon, cellulose ester, polyvinyl derivatives, polyolefins, polyamides, or polyesters, cuproammonium cellulose (Bemberg), natural materials such as wool, silk, jute, hemp, cotton, linen, sisal, ramie and combinations thereof. Furthermore, the chassis can comprise a variety of layers of various materials, and can be designed in specific shapes and orientations.

In order to impart added structure and further durability to the chassis, one or more optional stays can be included. The stays can serve as resilient stiffeners. For example, such stays may be embedded internally in the material of the chassis. Alternatively, the stays may be positioned on an outer surface of the chassis, away from the surface of the chassis that contacts a user's skin. Such stays can be formed from materials selected from the group consisting of bendable stripes of glue, polyethylene, polypropylene, rigid plastic, rigid metal, and combinations thereof.

The digit-receiving aperture(s) can be located on the body portion distal to a flexible retaining element. Alternatively, the digit-receiving aperture can be located proximal to the flexible retaining element. Alternatively there can be more than one digit-receiving aperture. The digit-receiving aperture(s) can be oriented in a transverse axis of the chassis, a longitudinal axis, and combinations thereof. The digit-receiving aperture(s) can be of varying shape and size, non-limiting examples of which include a slit and a slot, and combinations thereof, arcuate and non-arcuate shapes, and combinations thereof. The digit-receiving aperture(s) can be thumb-receiving apertures such that the thumb anchors the thermal covering in place during installation and use.

The chassis can also comprise a flexible retaining element. Non-limiting examples of a flexible retaining element include a single strap portion, two strap portions, and a plurality of strap portions. The flexible retaining element, when in the form of a strap or straps can be formed from an elastomeric material. Non-limiting examples of suitable elastomeric materials include elastomeric net (SCRIM), vacuum formed elastomers, and the like.

Attachment Element

The thermal covering of the present invention also includes at least one attachment element to releasably attach the thermal covering about a user's hand-wrist area, for example, using at least one strap portion and/or adhesive.

As used herein, the term "releasably attach" refers to that property which provides for initial permanent attachment of the strap portion(s) to the body portion of the chassis to secure the thermal covering around a user's hand-wrist area, and subsequent detachment of the strap portion(s) to allow removal of the thermal covering.

"Releasably attaching" also refers to the property which provides for initial securing of either a disposable or reusable thermic component to the chassis at the thermal region, and subsequent detachment of the thermic component from the chassis. The user may desire to release the thermal covering or thermic component and replace or reposition the thermal covering or thermic component as often as desired for optimal thermic delivery.

As used herein, the term "permanent attachment" refers to joining and securing the thermal covering about the hand-wrist area in such a manner that the thermal covering remains physically joined and secured about the hand-wrist area during ordinary use.

Such attachment element for securing the thermal covering about the hand-wrist area of a user can be integrated into the chassis and/or strap portion(s), or can be a separate component of a kit. The attachment element can be any of a variety of means for attaching, provided that the attachment is releasable. Accordingly, non-limiting examples of such attachment elements include: hook and loop systems, for example wherein such systems are integrated into the chassis and/or the flexible retaining element; or adhesives such as skin contact adhesives incorporated into the chassis and/or the flexible retaining element.

In an exemplary embodiment, the attachment element can include hook and loop fastening systems, for example VELCRO®. For example, the chassis can comprise a plurality of loop members which are formed from fibers of material. This plurality of loop members serves as one-half of a releasable hook and loop fastening system. The strap portion(s) can comprise a plurality of hook members which are releasably attachable to the loop members of the chassis. As such, the plurality of hook members serve as the second half of the attachment means.

The loop members can be formed from a variety of known materials. Particularly preferred loop members may comprise any warp or weft knit fabric having loops knitted therein, or nonwovens or nonwoven laminates capable of supporting hook attachment. An example material for the loop members includes an Aplix knitted loop available from Aplix, Charlotte, N.C.

Hook members can be any of a variety of styles, shapes, and/or densities depending upon the use. The hooks of hook members can be bent shafts, mushroom capped, harpoon-shaped, or any other suitable shape. The hooks of hook members can be unidirectional, bi-directional, or omni-directional depending upon the application and companion loops of the loop members. The hooks can comprise any of a variety of different materials, including polyethylene, polypropylene, nylon, polyester, styrene block copolymers, and the like. An example hook for use herein includes 960 polypropylene hooks, commercially available from Aplix, Charlotte, N.C. The hooks of hook members are chosen in conjunction with the companion loops of the loop members such as to provide peel and shear forces that are required for different applications. The ordinarily skilled artisan will recognize that a variety of other attachment means not explicitly described herein may be utilized.

In addition, optionally an adhesive, such as a skin contact adhesive, can be included, for example at least one adhesive region, to further help anchor the thermal covering on the hand-wrist area, particularly during installation or application of the thermal covering. A non-limiting example of an adhesive suitable for use on skin with the present invention is adhesive number 34-539B available from National Starch & Chemical Co., Bridewater, N.J.

The Thermic Component

The thermal covering of the present invention also comprises a thermic component. The thermic component is attachable, meaning either irreversibly incorporated into the chassis or removably attachable, to the chassis at the thermal region. In embodiments of the present invention, the thermic component of the invention can include at least about one heat cell formed integrally into the chassis, thereby creating a single use thermal covering. Alternatively the thermic component can be a separate component that itself can be disposable or reusable. If the thermic component is reusable, non-limiting examples include reusable heatable and reheatable thermic components, battery powered thermic components, electric powered thermic components, electromechanical thermic components, moisture-generating thermic components, and the like.

The thermic component utilized herein is suitable for providing heat or cold, as desired or needed, to the user's body when secured in place. In an embodiment of the present invention, a separate disposable thermic component comprises a heat pack comprising at least about one, including a plurality, of thermic cells, for example heat cells.

For example, a disposable thermic component, whether separate or integrated into the chassis, can comprise one or more heat cells comprising a thermoresponsive material, for example water, such as described in U.S. Pat. No. 2,602,302. Wherein the disposable thermic component comprises a thermoresponsive material, the disposable thermic component can be externally heated or cooled prior to use, as desired.

In one particular embodiment herein, the thermic component comprises at least about one thermic cells comprising an exothermic or endothermic composition, as applicable. In an embodiment of the invention having a disposable thermic component that is exothermic, and oxygen-activated, the disposable thermic component comprises a heat pack having a heat pack body and at least about one heat cell fixed integrally within or to the structure of the heat pack body. Wherein the heat cells(s) is fixed within the structure of the heat pack body, at least a portion of the heat pack body can be oxygen permeable.

In a particular embodiment of the present invention, disposable thermic components readily adaptable for use with the present invention are described in, for example, U.S. Pat. Nos. 6,020,040 and 6,146,732; and WO 98/29066. In a particular embodiment, the heat pack of the disposable thermic component comprises at least one continuous layer of a material, which preferably exhibits specific thermophysical properties, and a plurality of individual heat cells which comprise an exothermic composition, wherein the heat cells are spaced apart and fixed within or to the structure of the heat pack body, as described in the above patents and patent applications. Such heat cells can also be spaced apart and fixed within or to the structure of the chassis, at the thermal region if the entire thermal covering is to be disposable. Thus, the thermic component can be an integral part of chassis of the thermal covering such that the entire device is a single use, disposable device. Alternatively, the thermic component can be releaseably attachable to the chassis such that the chassis can be reused whether or not the thermic component is reusable.

Non-limiting examples of material suitable for the heat pack body include those listed above as suitable for the chassis body.

In an embodiment of the present invention, the disposable thermic component comprises a plurality of individual heat cells fixed within or to the material of the chassis body or the heat pack body. The heat cells are spaced apart from each other and each heat cell functions independently of the rest of the heat cells with respect to heat generation. While the heat cells can comprise any suitable composition for providing heat, such as exothermic compositions, microwavable compositions, heat of crystallization compositions and the like, an exemplary heat cell contains a densely packed, particulate exothermic composition that can shift only minimally within the heat cell. Alternatively, the exothermic composition can be compressed into a hard tablet or slug before being placed into each heat cell. The heat cells of the present invention can be present in any number, and can have any geometric shape, e.g., disk, triangle, square, cube, rectangle, cylinder, ellipsoid and the like, all or none of which may contain a hole or other reservoir through the middle of the cell. An example shape of the cell comprises an ellipsoid geometry. Alternatively, cells having geometric shapes other than an ellipsoid shape, for example, a disk shape can be used.

The heat cells can be integrally formed into the chassis or can be formed into a heat pack used separately and which is releasably attachable to the chassis of the present invention.

Composition

An embodiment of an exothermic composition, suitable for use with the thermal covering of the present invention, comprises a mix of chemical compounds that undergo an oxidation reaction during use. The compositions of the heat cells comprise a particulate premix and a brine solution. The particulate premix comprises iron powder, carbon, an absorbent gelling material, and water. The brine solution comprises a metal salt, water and optionally a hydrogen gas inhibitor such as sodium thiosulfate. Mixtures of this type react when exposed to oxygen, providing heat for several hours. Preferably, the exothermic composition comprises a particulate mix of chemical compounds that undergo an oxidation reaction during use. Alternatively, the exothermic composition may also be formed into agglomerated granules, direct compacted into compaction articles such as granules, pellets, tablets, and/or slugs, and mixtures thereof.

The exothermic compositions defined herein can be prepared by constructing the premix composition and rapidly dosing the premix with the brine solution. An example heat cell can comprise from about 0.4 grams of premix per cell to about 2.5 grams of premix per cell, and from about 0.4 grams of brine solution per cell to about 1.5 grams of brine solution per cell. Thus, an exothermic composition of the present invention can comprise a total cell weight, per cell, of from about 0.8 grams to about 4 grams, alternatively from about 1.5 grams to about 3.5 grams, and alternatively from about 2.5 grams to about 3 grams.

The exothermic compositions comprise at least about one iron powder component at concentrations of from about 10% to about 90%, alternatively from about 30% to about 90% and alternatively from about 50% to about 87%, by weight of the composition.

Non-limiting suitable sources for iron powder include cast iron powder, reduced iron powder, electrolytic iron powder, scrap iron powder, sponge iron, pig iron, wrought iron, various steels, iron alloys, treated varieties of the iron sources, and the like. There is no particular limitation to their purity, kind, and other properties, so long as the iron powder can be used to produce heat-generation with electrically conducting water and air.

The exothermic compositions also comprise at least about one carbon component at concentrations of from about 1% to about 25%, alternatively from about 3% to about 20%, and alternatively from about 3.5% to about 10%, by weight of the composition.

Carbonaceous materials and mixtures thereof can be used in the exothermic compositions. Non-limiting examples of carbon suitable for use in the compositions of the present invention include activated carbon, non-activated carbon, and mixtures thereof. Non-limiting examples of activated carbon include activated carbon prepared from coconut shell, wood, charcoal, coal, bone meal, but those prepared from other raw materials such as animal products, natural gas, fats, oils and resins are also useful in the particulate exothermic compositions of the present invention. There is no limitation to the kinds of activated carbon used. However, activated carbon has superior oxygen-adsorption capability. Different carbons also can be blended to reduce cost. Therefore, mixtures of the above carbons are useful in the present invention as well.

The exothermic compositions of the present invention also comprise an absorbent gelling material at concentrations of from about 1% to about 25%, alternatively from about 1% to about 15% and from about 1% to about 10%, by weight of the exothermic composition. The absorbent gelling material enables the retention of water physically or chemically within the particulate exothermic compositions, to gradually supply water to the iron powder component and a controlled rate.

Non-limiting examples of suitable absorbent gelling materials include those materials that have fluid-absorbing properties and can form hydrogels upon contact with water, such as that based on a polyacid such as polyacrylic acid. Examples of commercially available polyacrylate include those polyacrylates available from Nippon Shokubai located in Chatanooga, Tenn., USA.

The compositions of the present invention can also comprise water holding materials at concentrations of from about 0.1% to about 25%, alternatively from about 0.5% to about 20%, and alternatively from about 1% to about 15%, by weight of the composition. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts. Other porous materials having a large capillary function and hydrophilic property can also be used. Examples of absorbent gelling materials and water holding materials can be found in U.S. Pat. Nos. 5,918,590 and 5,984,995 as well as U.S. patent application Ser. No. 11/233,916.

The exothermic compositions of the present invention also comprise at least about one metal salt at concentrations of from about 0.5% to about 10%, alternatively from about 0.5% to about 7%, and alternatively from about 1% to about 5% by weight of the composition.

Non-limiting examples of metal salts useful in the particulate exothermic compositions include sulfates such as ferric sulfate, potassium sulfate, sodium sulfate, manganese sulfate, magnesium sulfate and mixtures thereof; and chlorides such as cupric chloride, potassium chloride, sodium chloride, calcium chloride, manganese chloride, magnesium chloride, cuprous chloride, and mixtures thereof. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof.

The particulate exothermic compositions of the present invention also comprise water at concentrations of from about 1% to about 35%, and alternatively from about 5% to about 33%, by weight of the composition.

The water used in the particulate exothermic composition may be from any appropriate source including, for example, tap water, distilled water, deionized water, and mixtures thereof. There is no particular limitation to its purity, kind, and the like.

Therefore, in a particular embodiment, a heat cell of the present invention can comprise a particulate exothermic composition wherein the particulate exothermic composition comprises (a) from about 10% to about 90% by weight of iron powder; (b) from about 1% to about 25% by weight of a carbon selected from the group consisting of activated carbon, non-activated carbon, and mixtures thereof; (c) from about 1% to about 25% by weight of an absorbent gelling material having a median particle size of from about 300 µm to about 800 µm; and (d) from about 1% to about 35% by weight of water; wherein the particles of the particulate exothermic composition are combined in a pocket, formed in a unified structure of a chassis body or a heat pack body, comprising at least two opposed surfaces, wherein at least one surface is oxygen permeable.

Optional Components

The thermal covering and thermic component of the present invention can optionally incorporate a component, such as a separate substrate layer or a component incorporated into the material of the chassis body or heat pack body, comprising active aromatic compounds, non-active aromatic compounds, pharmaceutical actives or other therapeutic agents, and mixtures thereof, to be delivered through the skin. Such active aromatic compounds include, but are not limited to, menthol, camphor, and eucalyptus, vanilla, lavender, and various essential oils that can be used for aromatherapy. Such non-active aromatic compounds include, but are not limited to, benzaldehyde, citral, decanal, and aldehyde. Such pharmaceutical actives/therapeutic agents include, but are not limited to antibiotics, vitamins, antiviral agents, analgesics, anti-inflammatory agents, antipruritics, antipyretics, anesthetic agents, antifungals, antimicrobials, and mixtures thereof. The thermic component can also comprise a sweat-absorbing component.

The above-mentioned components of the composition are blended using conventional blending techniques. Example suitable methods of blending these components are described in detail in U.S. Pat. No. 4,649,895.

The finished thermic components, if using oxygen-activated compositions, whether separate disposable thermic components, or whether formed integrally into the chassis, can be packaged in a secondary air-impermeable package to prevent an oxidation reaction from occurring until desired, such as described in U.S. Pat. No. 4,649,895. Alternatively, other means can also be used to prevent an oxidation reaction from occurring before desired, such as air impermeable removable adhesive strips can be placed over the heat cells such that, when the strips are removed, air is allowed to enter the heat cell, thus activating the oxidation reaction of the iron powder.

Securing Element for Attaching a Thermic Component

The present invention can also include an element for securing a thermic component to the chassis, if the thermic component is releasably attachable to the chassis. The securing element can be any of a variety of means for attaching, provided that the thermal covering and/or thermic component can be subsequently released. Accordingly, non-limiting examples of such means include: hook and look systems, for example wherein such systems are integrated into the chassis and the thermic component; or adhesives such as pressure sensitive adhesives.

In an exemplary embodiment, the attachment means can include hook and loop fastening systems, for example VELCRO®. For example, the chassis can comprise a plurality of loop members which are formed from fibers of material. This plurality of loop members serves as one-half of a releasable hook and loop fastening system. The thermic component, whether reusable or disposable, can comprise a plurality of hook members which are releasably attachable to the loop members of the chassis. As such, the plurality of hook members serve as the second half of the attachment means.

The loop members can be formed from a variety of known materials. Particularly preferred loop members can comprise any warp or weft knit fabric having loops knitted therein, or nonwovens or nonwoven laminates capable of supporting hook attachment. An example material suitable for the loop members includes an Aplix knitted loop commercially available from Aplix, Charlotte, N.C.

Hook members can be any of a variety of styles, shapes, and/or densities depending upon the use. The hooks of hook members may be bent shafts, mushroom capped, harpoon-shaped, or any other suitable shape. The hooks of hook members can be unidirectional, bidirectional, or omni-directional depending upon the application and companion loops of the loop members. The hooks can comprise any of a variety of different materials, including polyethylene, polypropylene, nylon, polyester, styrene block copolymers, and the like. An example hook for use herein includes 960 polypropylene hooks, commercially available from Aplix, Charlotte, N.C. The hooks of hook members are chosen in conjunction with the companion loops of the loop members such as to provide peel and shear forces that are required for different applications. The ordinarily skilled artisan will recognize that a variety of other attachment means not explicitly described herein may be utilized.

Alternatively, the means for releasably securing the thermic component to the chassis can include narrow pressure sensitive adhesive strands or fibrils attached to an outer surface of the thermic component. For example, the thermic component can comprise release paper attached to adhesive strands on the outer layer of the thermic component in order to protect the adhesive strands from prematurely adhering to a target other than the intended chassis. Such means preferably has a stronger bond to the outer surface of the thermic component than to either the release paper or, upon use, to the target chassis surface. This may optionally be achieved by melting the adhesive into the material of the outer surface of the thermic component such that mechanical entanglement occurs.

In a particular embodiment, a preferred cloth-fastening adhesive is product number 70-4595 pressure sensitive hot melt adhesive, commercially available from National Starch and Chemical Company of Bridgewater, N.J. As an example, this adhesive may be applied to the outer surface of the thermic component at about 25 grams per square meter (gsm) by spraying; alternatively the adhesive can also be applied by printing or slot coating. In either case it is desirable that the adhesive penetrate into the outer surface of the thermic component such that the adhesive preferentially adheres to the outer surface of the thermic component upon removal of the device from the body compress subsequent to use. The pattern of adhesive produced by this method may be straight parallel stripes extending from the edges of the thermic component. The release paper then utilized is preferably a silione treated paper, such as 24 KSD release paper, commercially available from Tekkote of Leonia, N.J.

Kits

The present kits include those comprising:
(a) a reusable chassis having a longitudinal axis and a transverse axis and comprising a flexible body portion having a single thermal region, wherein said body portion comprises a digit-receiving aperture through said body portion and adjacent to said thermal region; and
(b) a thermic component attachable to said body portion at said thermal region.

The kits can comprise any number of reusable chassis components and any number of disposable or reusable thermic components, as desired. Since the chasses are intended to be reused, typical kits can comprise, for example, one reusable chassis and at least about one, or a plurality, of disposable or reusable thermic components. This is convenient for the user, who can choose to use the reusable chassis on multiple occasions, but dispose of a given disposable thermic component subsequent to expenditure of that component.

In various embodiments described below, each reusable chassis and each thermic component can be separately contained each in a secondary package, and then packaged together as a single kit. In embodiments of the present invention wherein the disposable thermic component includes an oxygen-activated exothermic composition, each disposable thermic component can be packaged separately in oxygen-impermeable packaging until use.

The kits of the present invention can also include a flexible sleeve to secure the thermal covering on the user's hand-wrist area. The sleeve can have a digit-receiving aperture formed therein. The sleeve comprises an interior, a first end and a second end, both of which are open. To use the sleeve, a user slides the sleeve over the hand and wrist, inserting a thumb, if desired, through the digit-receiving aperture to help hold the sleeve in position. The sleeve can be comprised of any stretch material including, but not limited to, natural, reclaimed and synthetic rubbers; styrene block copolymers; polyurethane; metallocene-catalyzed polyethylene; and the like. These materials can optionally include foams; nonwoven materials; knits; films; elastomeric scrims, films, strands, ribbons, tapes; laminates of nonwovens and the aforementioned materials; and the like.

Packaging for the kit may be any of a variety of types, for example, a carton or box containing the members of the kit. The kit can also include usage instructions selected from the group consisting of: written instructions, pictorial instructions, and combinations thereof, in one or more languages.

Methods of the Invention

A method of the invention comprises the mammalian user removing the thermal covering from its packaging and applying the thermal covering to the hand-wrist area and securing the thermal covering around the hand-wrist area using the attachment element of the flexible retaining element, wherein the front of the thermic device is proximal to the surface of the user's skin such that the user can perform ordinary daily activities. Various embodiments of the thermal covering can be applied with one hand. If desired, a reusable sleeve can be applied. If heat cells are used, over about a twenty minute period, the heat cells present in the disposable thermic component, whether a separate component or formed integrally into the chassis, warm the disposable thermic component to result in a soothing skin temperature of about 34° C. to 43° C., alternatively from about 39° C. to 41° C. After up to about 8 to about 24 hours, the exothermic composition of the heat cells is substantially expended.

After the thermic device, which can be disposable or reusable, is expended or has cooled, the mammalian user removes the sleeve, if used, and the chassis from the hand-wrist area. If the user is using a thermal covering of the present invention with the heat cells formed integrally into the chassis, the entire chassis including the integrally formed thermic component are disposed of. If the user is using a reusable chassis and releasable thermic component, the mammalian user removes the thermal covering from the hand-wrist area and disposes of the expended thermic device, or stores, reheats, or recharges the thermic device if the thermic device is reusable. The reusable chassis portion of the thermal covering can be washed and used again with new disposable thermic devices or reheated reusable thermic devices, or can be stored for future use.

Non-limiting Embodiments of the Thermal Covering

The following provides non-limiting examples of embodiments of the present invention. For example, a kit comprising one reusable chassis and four releasably disposable thermic components is provided to a mammalian user. Each of the four disposable thermic components is separately packaged in a secondary package to inhibit initiation of the exothermic reaction until desired use.

Figure 1:
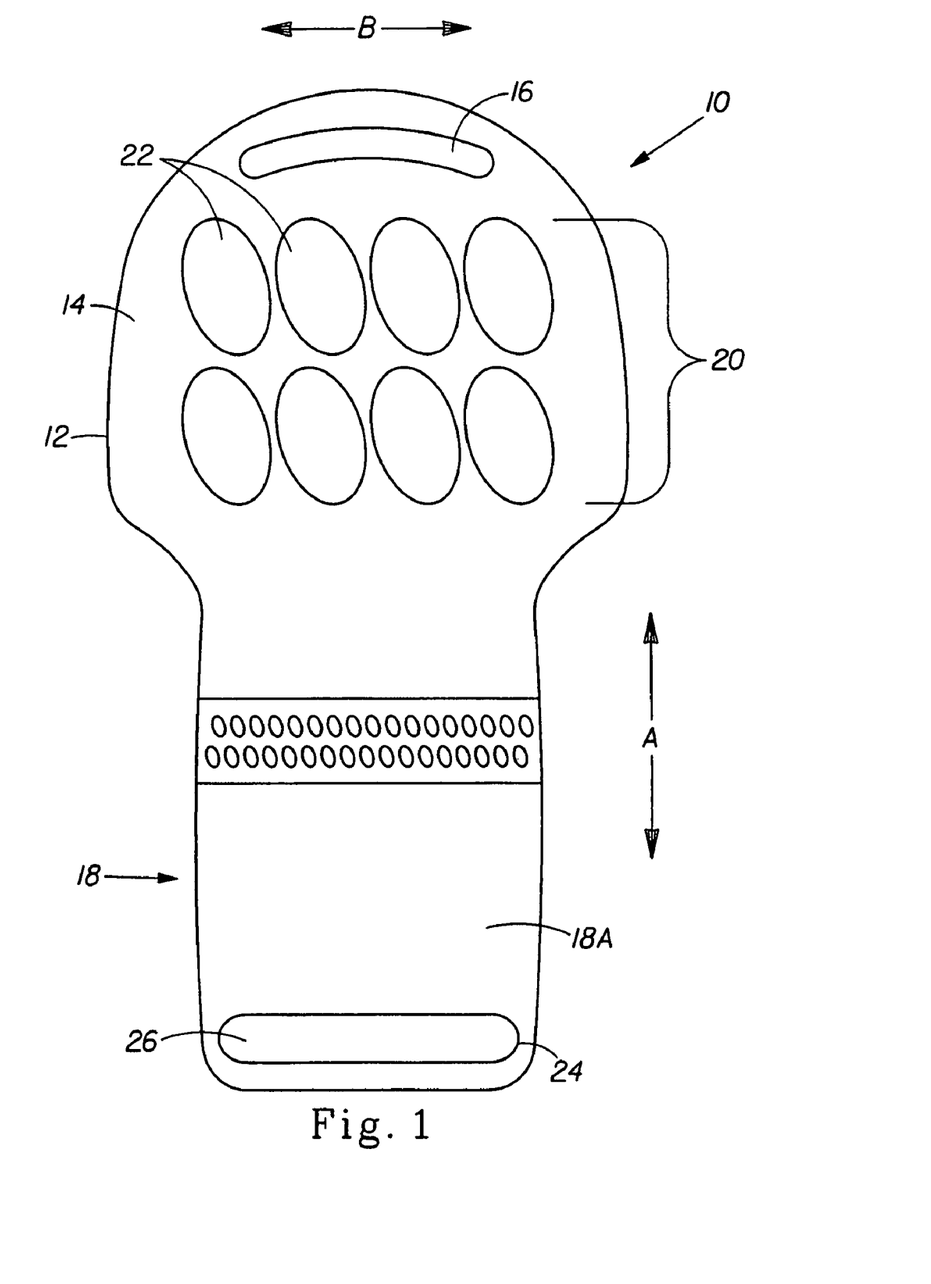
FIG. 1 is a front plan view of an embodiment of a thermal covering of the present invention.

FIG. 1 shows a fully disposable embodiment of the invention comprising a chassis 10 having a longitudinal axis A and a transverse axis B and comprising a flexible body portion 12 having at least one thermal region 14, wherein the body portion 12 comprises an arcuate digit-receiving aperture 16 through the body portion 12, and adjacent to the thermal region 14. The present invention can also comprise a flexible retaining element 18; wherein at least one of the body portion 12 and the flexible retaining element comprises 18 an elastomeric material, and wherein at least one of the body portion 12 and the flexible retaining element 18 is stretchable along the longitudinal axis A of the chassis 10. A digit-receiving aperture 16 is shown distal to the retaining element. The present invention also comprises a thermic component 20 attachable and integrally formed into the body portion 12 at said thermal region 14, and comprising a plurality of heat cells 22 formed integrally into the chassis 10. Also shown is a single strap portion 18a as the flexible retaining element, which is stretchable. Single strap portion 18a comprises an attachment means 24 comprising in this example, a hook and loop fastening system, the hook portion of which is shown at reference numeral 26. The chassis 10, as noted above, can include loop material to which the hook portion 26 can attach to secure the thermal covering to a user's hand-wrist area.

Figure 2:
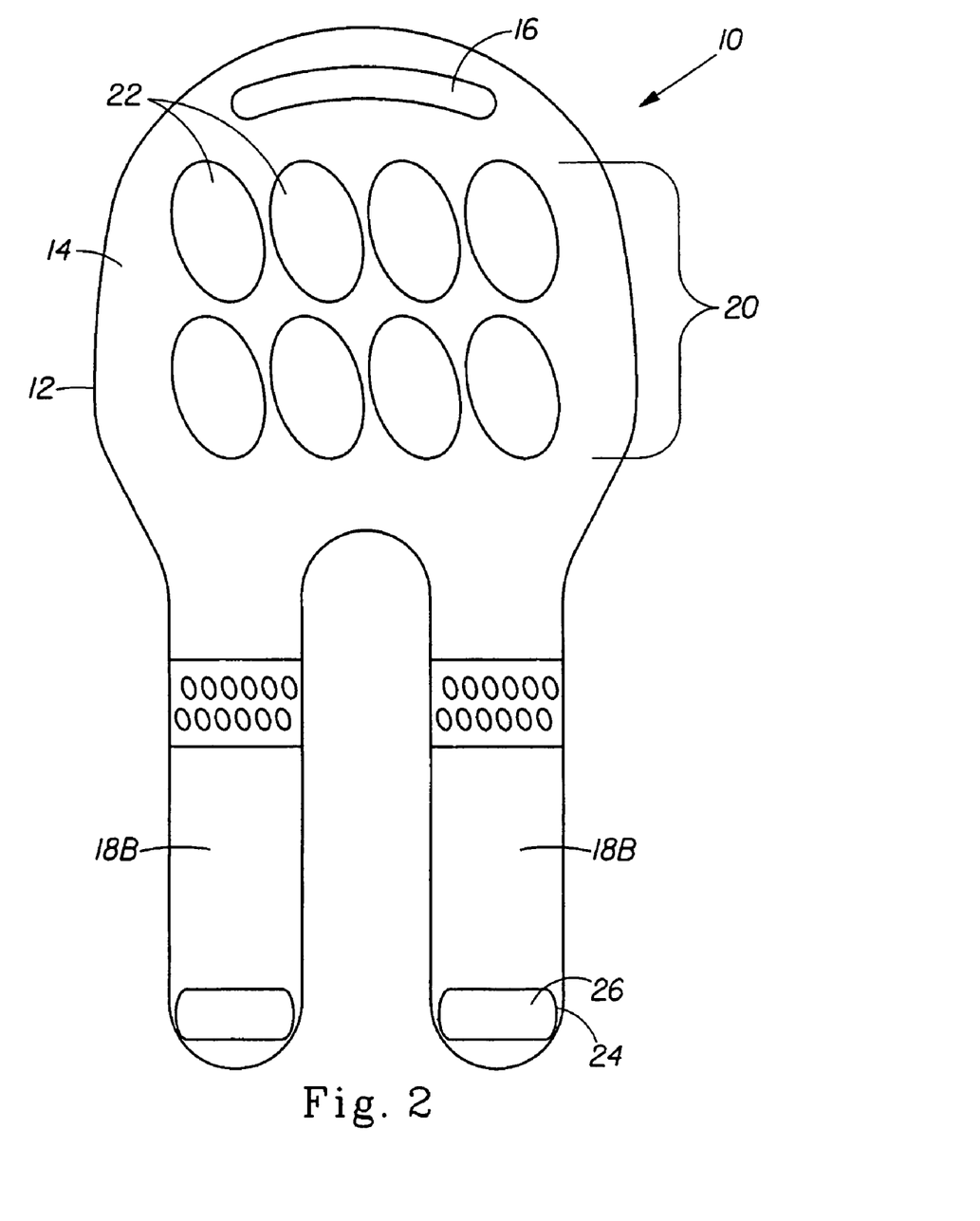
FIG. 2 is a front plan view of an alternative embodiment of a thermal covering of the present invention.

FIG. 2 illustrates an embodiment of the invention having two strap portions 18b each of which is stretchable and each of which has an attachment means 24 hook portion 26 thereon. Also shown is a plurality of heat cells 22 integrally formed into chassis 10, and an arcuate digit-receiving aperture 16 distal to the strap portions 18b.

Figure 3:
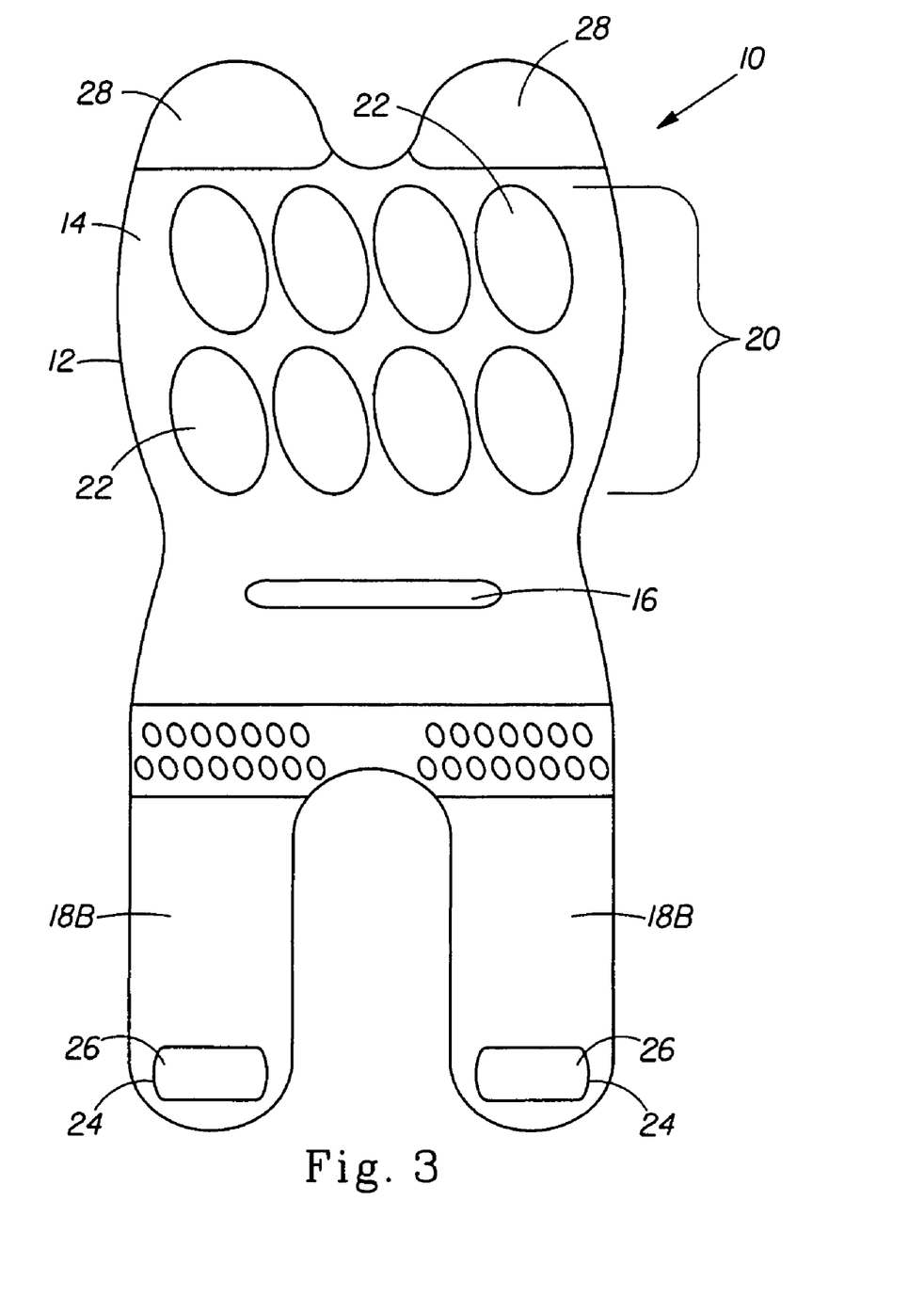
FIG. 3 is a front plan view of another embodiment of a thermal covering of the present invention.

FIG. 3 illustrates yet another embodiment of the present invention having two strap portions 18b, a plurality of heat cells 22 integrally formed into chassis 10, and a non-arcuate digit-receiving aperture 16 proximal to the strap portions 18b. Also included in this embodiment are two areas of skin attachable adhesive 28, used to aid in the application or installation of the thermal covering.

Figure 4:
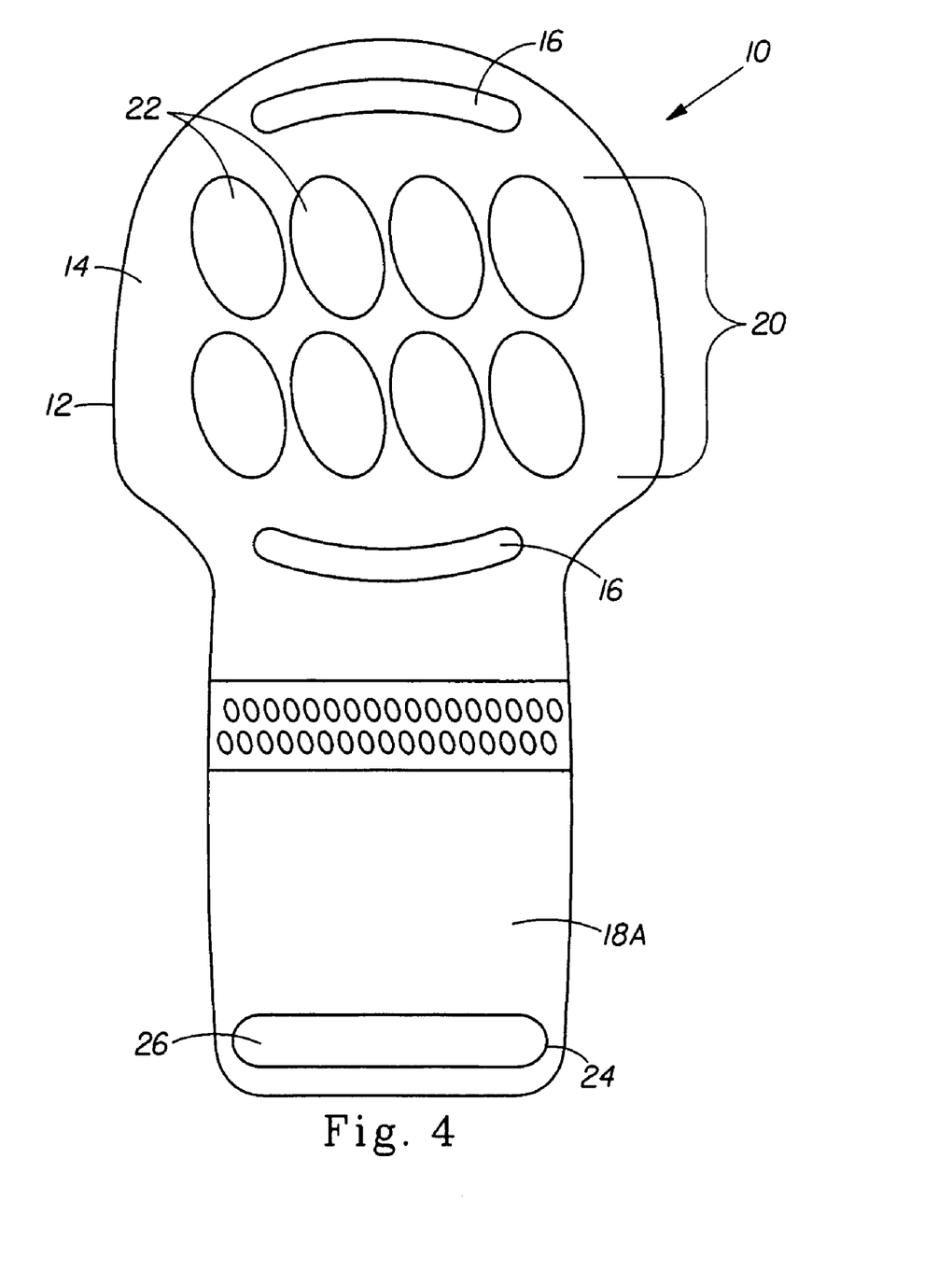
FIG. 4 is a front plan view of an additional embodiment of a thermal covering of the present invention.

FIG. 4 illustrates an embodiment having a single strap portion 18a and two arcuate digit-receiving apertures 16.

Figure 5:
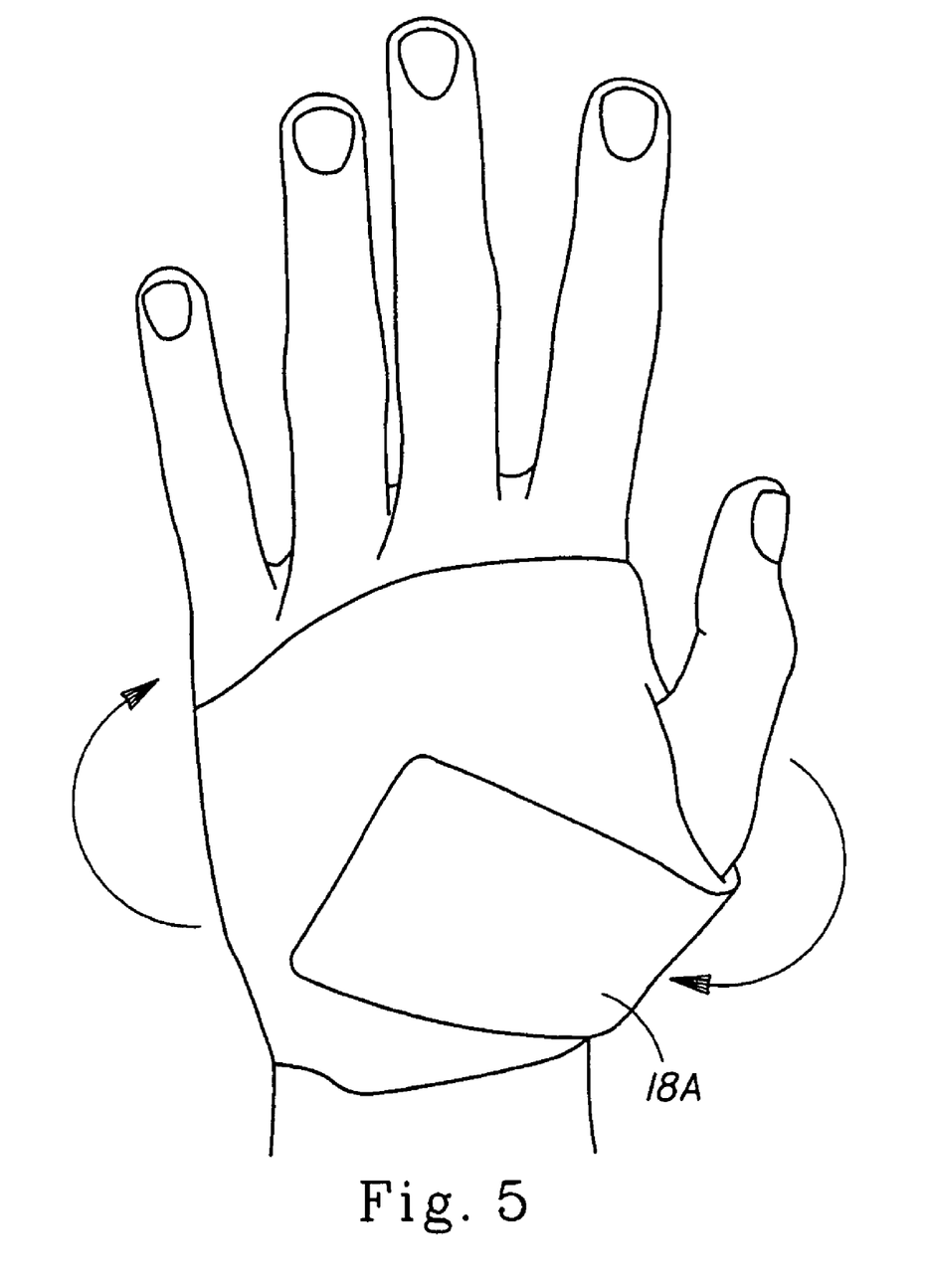
FIG. 5 is a front plan view of an embodiment of the present invention.

FIG. 5 illustrates a thermal covering of the present invention in use wrapped about a user's hand-wrist area. The heat cells are not shown as they are located on the front or skin side of the thermal covering.

Figure 6:
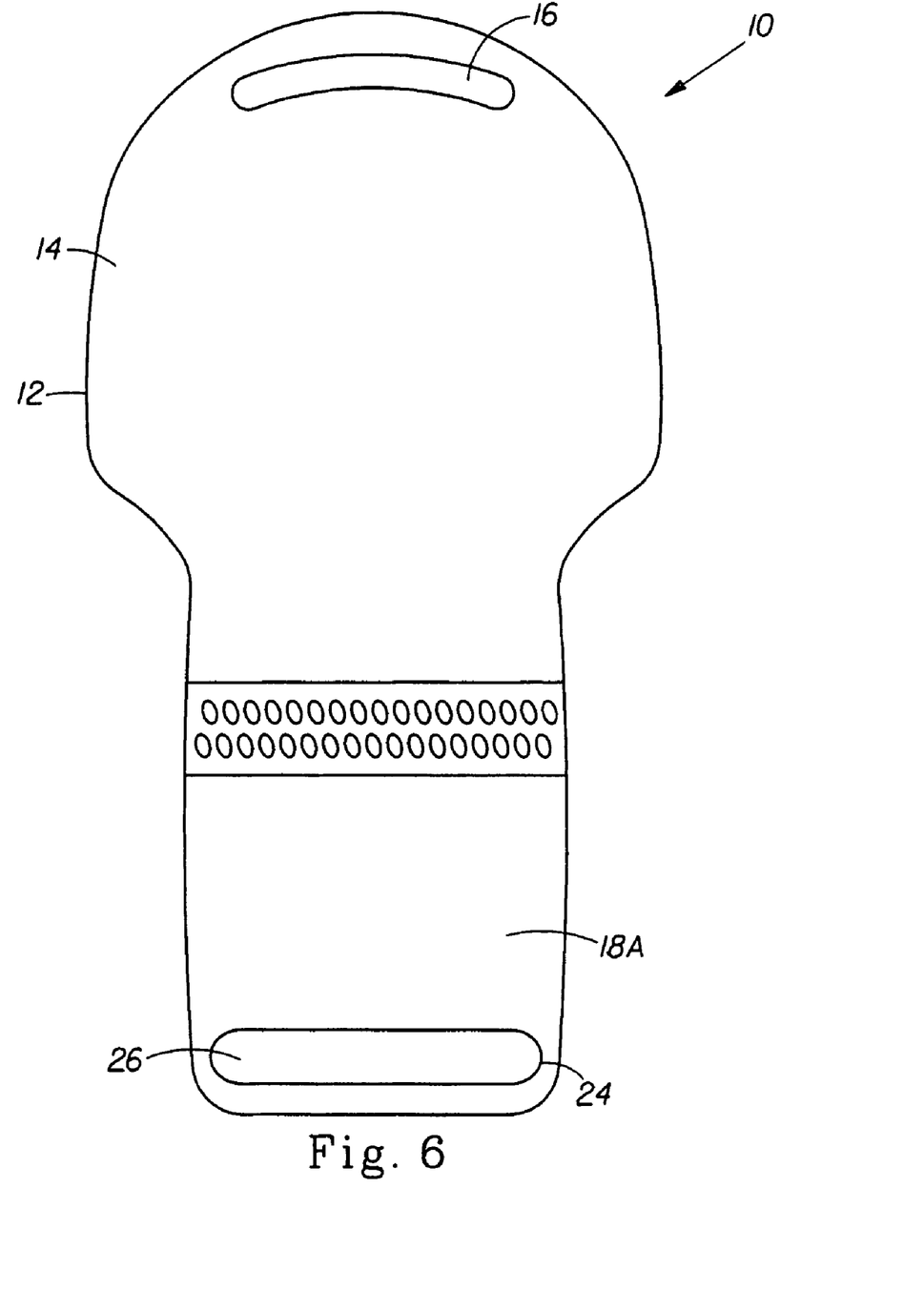
FIG. 6 is a front plan view of an alternative embodiment of the present invention.

FIG. 6 illustrates a reusable chassis 10 of the present invention. Flexible body portion 12 includes thermal region 14 wherein a releaseably attachable thermic component is attachable. A single strap portion 18a is shown with hook portion 26 of an attachment means 24. The chassis of this particular embodiment has a single arcuate digit-receiving aperture 16.

Figure 7:
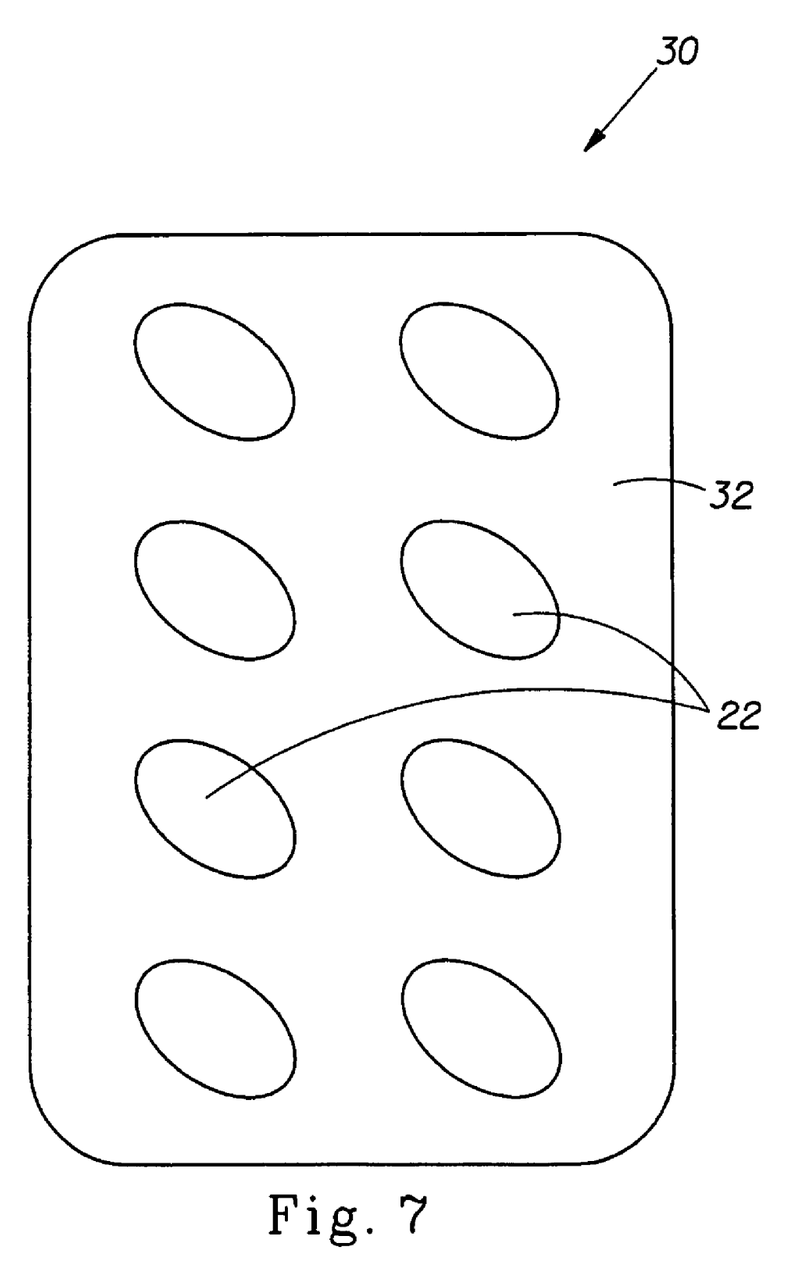
FIG. 7 is a front plan view of an embodiment of a disposable heat pack usable with a reusable chassis.

FIG. 7 illustrates a disposable heat pack 30 for use with a reusable chassis 10 such as that shown in FIG. 6. The heat pack 30 comprises a heat pack body 32, and is releasably attachable to the flexible body portion 12 of the chassis 10 at thermal region 14, and comprises a plurality of heat cells 22.

Figure 8:
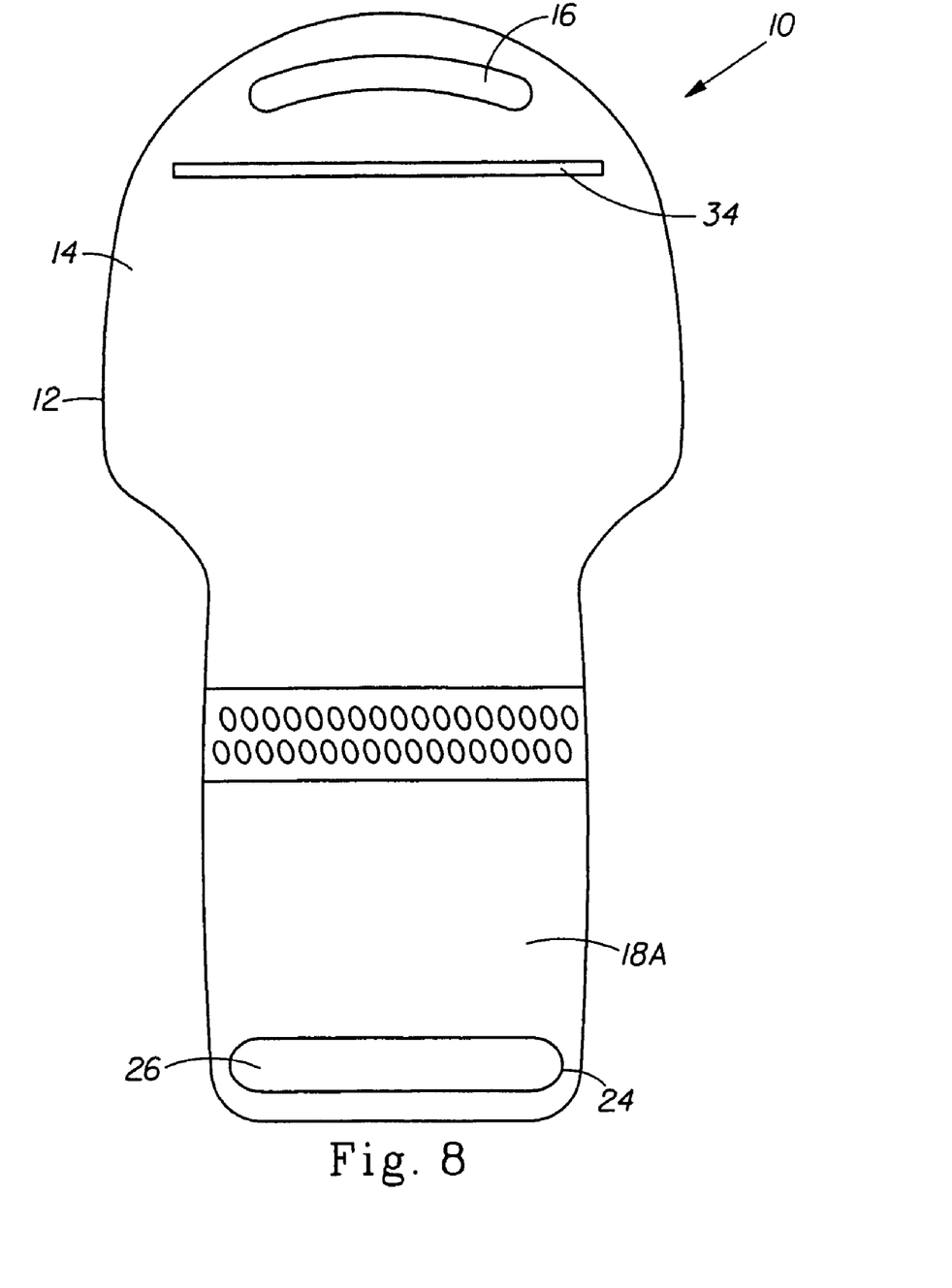
FIG. 8 is a front plan view of an embodiment of a reusable chassis having a pouch therein.

FIG. 8 illustrates yet another embodiment of a reusable chassis 10 of the present invention. In this example, chassis 10, has a pocket 34 formed therein, in which a heat pack such as that shown in FIG. 7 could be inserted, and thus be releasably attached to the chassis 10.

Figure 9:
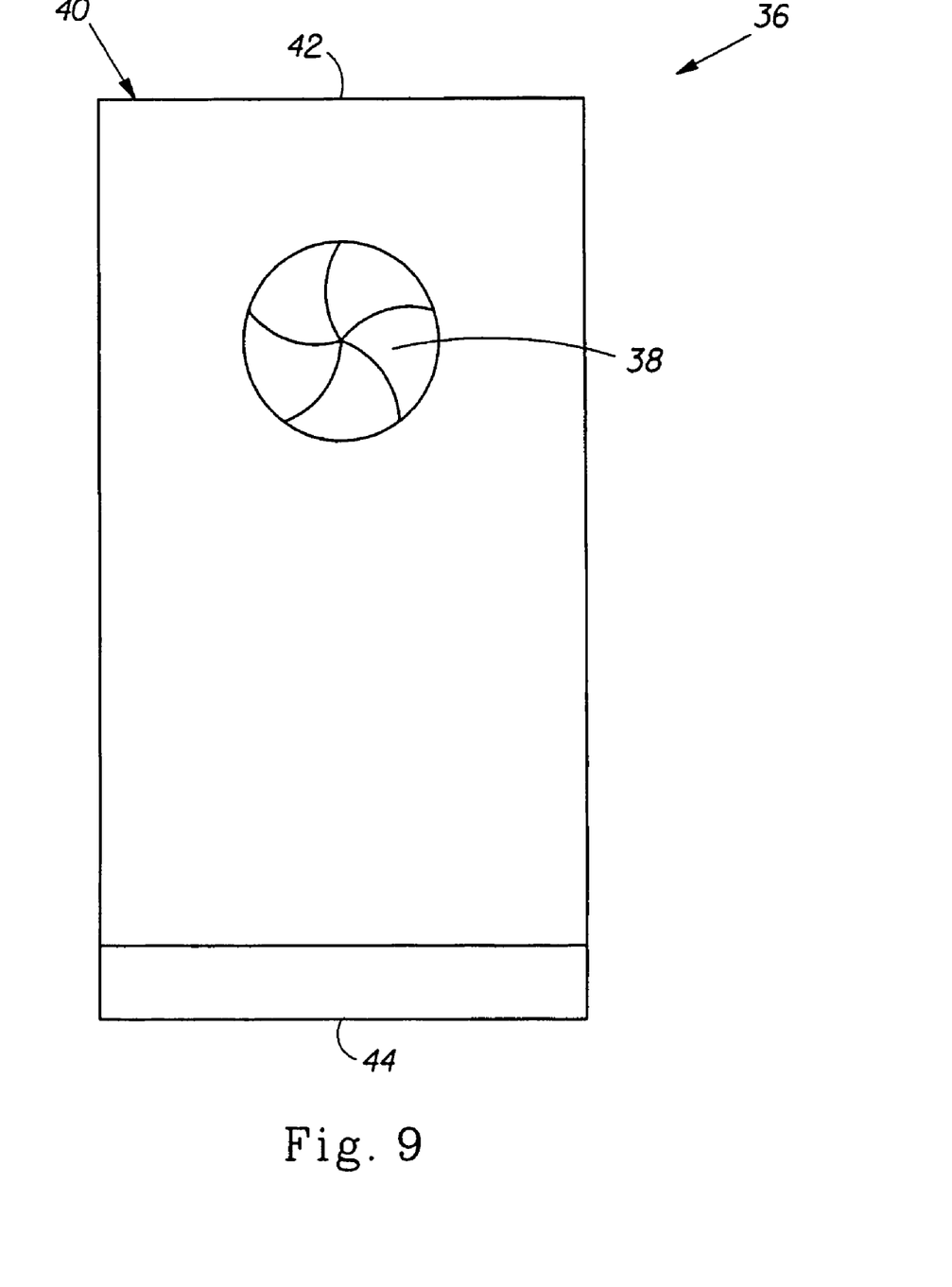
FIG. 9 is a front plan view of an embodiment of a sleeve of the present invention.

FIG. 9 illustrates an optional flexible sleeve 36. Sleeve 36 has a digit-receiving aperture 38 formed therein. Sleeve 36 comprises an interior 40, a first end 42 and a second end 44, both of which are open. To use the sleeve 36, a user slides sleeve 36 over the hand and wrist, inserting a thumb, if desired, through aperture 38 to help hold sleeve 36 in position.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

The following is an example of an embodiment of the thermal covering of the present invention:

1. To begin forming the chassis, start with a base layer of a polypropylene carded non-woven, (for example material number 6780 available from PGI, Inc.) at 22 grams per square meter (gsm).

2. Apply a hot melt construction adhesive for example spirally applied at 15 grams per square meter, (available as adhesive number 70-4589 from National Starch & Chemical Company) to one entire surface of the non-woven.

3. Apply a thermic component, in this example a heat pack, made as described in the example below, to the adhesive on the non-woven part of the chassis. The heat pack is applied at the thermal region of the chassis as described in the Fig.'s above.

4. Apply a flexible, elastomeric laminate material to the non-woven part of the chassis, adjacent to the thermal region to form a strap portion attached at one end and free at the other. The flexible, elastomeric laminate can be Conwed product number X500 20-002 bonded between two layers of a non-woven such as the PTI 6780 used in #1 above.

5. Apply 15 gsm construction adhesive (same as #2 above) to the top surface of the heat pack.

6. Apply as a top layer of the chassis of the thermal covering, a laminate over the heat pack and thermal region and overlapping about one inch onto the flexible elastomeric material of the strap. The laminate can be from Aplix, for example product number AN-35WH.

7. Apply an attachment element such as the hook portion of a hook and loop fastener to the free end of the elastomeric laminate material strap portion. The hook material can be Aplix 13 mm wide hook material number 960 that is pre-coated with adhesive.

8. Optionally apply a skin contact adhesive component to an adhesive region(s) of the chassis, distal to the strap portion. The skin contact adhesive can be slot coated to the designated non-woven part of the chassis, and covered with a peel paper (for example Tekkote paper number SAG24KSB) which the user removes when attaching the thermal covering to the user's skin.

9. Ultrasonically bond all overlapping portions of the materials to form a complete thermal covering comprising an integrated heat pack.

10. Cut overall thermal covering to desired shape.

11. Package the finished thermal covering with integrated thermic component in an oxygen-impermeable package to prevent initiation of the exothermic reaction.

An example heat pack, whether integrated into a thermal covering or left separate and removably attachable to a chassis of the thermal covering, is made as follows:

1. Start with a base layer of non-apertured 1 mil ($\frac{1}{1000}^{th}$ inch) thick 60% polypropylene/40% EVA (ethylene vinyl acetate) film number DH245 available from Clopay Plastics Products.

2. Place the film over a forming plate, with the EVA side of the base layer facing up, the plate having openings therein shaped and sized as desired for each heat cell.

3. Draw a vacuum on the film such that the film is drawn down into the openings to form pockets.

4. Add about 2.2 grams of the particulate exothermic composition described above into each pocket.

5. Add 0.9 grams of the brine solution described above to each pocket containing the particulate exothermic composition.

6. Apply a top layer of apertured 1 mil thick 60% polypropylene/40% EVA film with the EVA side down, facing the heat cells. The apertures of this layer are formed by hot needles, and provide oxygen permeability.

7. Heat seal the heat pack together.

All documents cited in the Detailed Description of the Invention are, in relevant part, incorporated herein by reference. The citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such modifications that are within the scope of this invention.

What is claimed is:

1. A thermal covering for use on the hand-wrist area of a user comprising:
   (a) a chassis having a longitudinal axis and a transverse axis and comprising a flexible body portion having at least one thermal region;
   (b) a thermic component irreversibly incorporated into said body portion at said thermal region wherein said thermic component comprises at least one continuous layer of material and a plurality of individual heat cells spaced apart and fixed to the at least one continue layer of material, said thermic component being integral with said chassis; and
   (c) a digit-receiving aperture through said body portion and adjacent to said thermal region;
   (d) a releasable attachment element to releasably attach the thermal covering around the hand-wrist area of the user.

2. The thermal covering of claim 1 further comprising a flexible retaining element.

3. The thermal covering of claim 2 wherein at least one of said body portion and said flexible retaining element comprises an elastomeric material; and wherein at least one of said body portion and said flexible retaining element is stretchable along said longitudinal axis of said chassis.

4. The thermal covering of claim 3 wherein said flexible retaining element comprises at least one strap portion fixedly attached to said body portion adjacent to said thermal region, and wherein said strap portion comprises an attachment element.

5. The thermal covering of claim 3 wherein said flexible retaining element comprises two strap portions fixedly attached to said body portion adjacent said thermal region.

6. The thermal covering of claim 2 wherein said digit-receiving aperture is oriented in a transverse axis of said chassis and is located distally from said retaining element.

7. The thermal covering of claim 1 comprising a plurality of digit-receiving apertures.

8. The thermal covering of claim 1 wherein said digit-receiving aperture is selected from the group consisting of a slit, a slot, and combinations thereof.

9. A thermal covering kit comprising: (a) a chassis having a longitudinal axis and a transverse axis and comprising a flexible body portion having at least one thermal region integral with said chassis, wherein said body portion comprises a digit-receiving aperture through said body portion and adjacent to said thermal region; (b) a thermic component irreversibly incorporated into said body portion at said thermal region, wherein said thermic component comprises at least one continuous layer of material and a plurality of individual heat cells spaced apart and fixed to the at least one continuous layer of material; and (c) a releasable attachment element to releasably attach the thermal covering around the hand-wrist area of a user, wherein the thermal covering is packaged in a removable air-impermeable package.

10. The kit of claim 9 further comprising a flexible retaining element, wherein at least one of said body portion and said flexible retaining element comprises an elastomeric material, and wherein at least one of said body portion and said flexible retaining element is stretchable along said longitudinal axis of said reusable chassis.

11. The kit of claim 9 wherein said digit-receiving aperture is oriented in a transverse axis of said chassis and oriented distally from said retaining element.

12. The kit of claim 9 further comprising usage instructions selected from the group consisting of: written instructions, pictorial instructions, and combinations thereof.

13. The kit of claim 9 further comprising a sleeve having an interior, an open first end and an open second end, wherein said sleeve further comprises a digit-receiving aperture through which a user's thumb is insertable, and wherein said sleeve comprises material selected from the group consisting of: bandage wrap materials, natural rubbers; reclaimed rubbers; synthetic rubbers; styrene block copolymers; polyurethane; metallocene-catalized polyethylene; foams; knits; films; elastomeric scrims, strands, ribbons, tapes; non-woven materials; laminates of non-wovens and the preceding materials; and combinations thereof.

* * * * *